(12) United States Patent
Ibrahim et al.

(10) Patent No.: US 12,275,003 B1
(45) Date of Patent: Apr. 15, 2025

(54) CARBON-SUPPORTED COPPER MANGANITE NANOPARTICLES FOR BIOFUEL PRODUCTION

(71) Applicant: IMAM MOHAMMAD IBN SAUD ISLAMIC UNIVERSITY, Riyadh (SA)

(72) Inventors: Mohamed Nady Abd El-Hameed Ibrahim, Riyadh (SA); Abd El-Aziz Ahmed Said, Assiut (EG)

(73) Assignee: IMAM MOHAMMAD IBN SAUD ISLAMIC UNIVERSITY, Riyadh (SA)

( * ) Notice: Subject to any disclaimer, the term of this patent is extended or adjusted under 35 U.S.C. 154(b) by 0 days.

(21) Appl. No.: 18/971,324

(22) Filed: Dec. 6, 2024

(51) Int. Cl.
*B01J 23/84* (2006.01)
*B01J 21/18* (2006.01)
(Continued)

(52) U.S. Cl.
CPC .............. *B01J 23/84* (2013.01); *B01J 35/397* (2024.01); *B01J 35/45* (2024.01); *B01J 37/04* (2013.01);
(Continued)

(58) Field of Classification Search
CPC ........ B01J 23/84; B01J 23/8892; B01J 35/45; B01J 35/397; B01J 37/04; B01J 37/086;
(Continued)

(56) References Cited

U.S. PATENT DOCUMENTS 3,904,553 A * 9/1975 Campbell ................ B01J 37/08
502/316
2010/0226845 A1* 9/2010 Hutchings .............. B01J 35/393
977/773
(Continued)

FOREIGN PATENT DOCUMENTS

CN 100360228 C 1/2008
CN 1101262 C 2/2009
(Continued)

OTHER PUBLICATIONS

P. Deva et al., "Facile synthesis of CuMn2O4 nanoparticles for efficient high performance electrode materials for supercapacitor application." Ceramics International 50, pp. 11916-11927. (Year: 2024).*

(Continued)

*Primary Examiner* — Patricia L. Hailey
(74) *Attorney, Agent, or Firm* — Oblon, McClelland, Maier & Neustadt, L.L.P.

(57) ABSTRACT

A method of preparing nanoparticles of carbon-supported copper manganite ($CuMn_2O_4$) comprising: preparing a first solution of a copper (II) salt and a manganese salt in a first polar organic solvent, where the molar ratio of Cu:Mn is from about 0.8:1 to about 1.2:1; admixing a second solution containing an organic ligand in a second polar organic solvent with the first solution to form a first mixture, wherein the second polar organic solvent is miscible with the first polar organic solvent; hydrothermally heating the obtained mixture at a temperature of from about 100° C. to about 200°

(Continued)

C. for a duration sufficient to yield a solid metal-organic framework composite material; and, calcining the composite material at a temperature in the range of from about 350° C. to about 600° C.

19 Claims, 7 Drawing Sheets

(51) Int. Cl.
*B01J 35/30* (2024.01)
*B01J 35/45* (2024.01)
*B01J 37/04* (2006.01)
*B01J 37/08* (2006.01)
*C07C 45/00* (2006.01)

(52) U.S. Cl.
CPC ........... *B01J 37/086* (2013.01); *C07C 45/002* (2013.01); *B01J 21/18* (2013.01)

(58) Field of Classification Search
CPC ....... B01J 21/18; B01J 21/005; C07C 45/002; C01P 2002/32
USPC ........................... 502/324, 524, 184; 585/252
See application file for complete search history.

(56) References Cited

U.S. PATENT DOCUMENTS

| | | | | |
|---|---|---|---|---|
| 2013/0161574 A1* | 6/2013 | Feltz | ...................... | C04B 35/622 |
| | | | | 252/519.15 |
| 2016/0082422 A1* | 3/2016 | Nazarpoor | ............. | B01J 23/745 |
| | | | | 502/331 |
| 2023/0261211 A1* | 8/2023 | Fang | ...................... | H01M 8/083 |
| | | | | 429/528 |

FOREIGN PATENT DOCUMENTS

| | | | | |
|---|---|---|---|---|
| CN | 113830749 A | * | 12/2021 | ............ B01J 23/755 |
| CN | 114192156 A | | 3/2022 | |
| KR | 10-1059885 B1 | | 8/2011 | |

OTHER PUBLICATIONS

Li Zhang, et al., "Preparation and catalytic performance of the copper-manganese-silicon catalysts for dehydrogenation reaction of 2-butanol", Journal of the Chemical Society of Pakistan, vol. 48, No. 01, 2024, pp. 16-28, (11 pages).

* cited by examiner

CARBON-SUPPORTED COPPER MANGANITE NANOPARTICLES FOR BIOFUEL PRODUCTION

STATEMENT OF ACKNOWLEDGEMENT

Support provided by the Imam Mohammad Ibn Saud Islamic University (IMSIU) is gratefully acknowledged.

BACKGROUND

Technical Field

The present disclosure is directed towards biofuel catalysts, and more particularly, towards a method of fabricating carbon-supported copper manganite (CuMn$_2$O$_4$@C) nanoparticles which may have utility as a catalyst for generating methyl ethyl ketone (MEK) by the dehydrogenation of butan-2-ol.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

With the advent of civilization, energy demand has increased exponentially, increasing the dependence of society on fossil fuels. However, as commonly known, fossil fuels are a finite resource and a polluting source of energy. Hence, the requirement for renewable energy resources is rapidly growing. Presently, several renewable energy sources are being used, such as, but not limited to solar energy, wind energy, geothermal energy, and hydroelectrical energy. However, the reliance on such renewable energy sources may not be economically viable in certain situations and/or may not be able to meet the requisite energy demand. Further, the storage of energy derived from such renewable sources remains a significant challenge due to the reliance on expensive, degradable batteries that require frequent replacement, resulting in higher long-term costs and environmental waste.

This situation has led researchers to investigate alternative fuel energy options, such as biofuels. In general, biofuels refer to any fuel that is derived from biological sources, typically organic matter such as plants, algae, and animal waste. Biofuels are produced through processes that convert biomass into usable energy forms, such as liquid fuels, gases, or solid fuels. Biofuels are considered a renewable energy source due to the ability of biofuels to be replenished over time through natural processes. Biofuels are presently used in transportation, heating, and electricity generation, serving as alternatives to or supplements of fossil fuels.

An exemplary biofuel is methyl ethyl ketone (MEK, butan-2-one), which is a next-generation biofuel option which may have utility in spark-ignition engines on account of its high octane number. In other implementations, MEK may be used as a solvent in adhesives, printing inks, and as a lubricant oil in dewaxing processes. Furthermore, MEK may be used for vegetable oil extraction, for sterilization of medical tools and as precursor for 2,2'-peroxydi(butane-2-peroxol).

According to public domain data, by 2020, MEK output around the world had surpassed 1.7 million tons and it is anticipated that the MEK market may grow further. There are, however, certain challenges in traditional manufacturing processes of MEK, specifically low yields and the concomitant generation of environmental pollutants. It is therefore considered that a need exists for an efficient method of producing MEK using nano catalysts.

Accordingly, it is one object of the present disclosure to provide a method of generating MEK using, as catalyst, carbon-supported copper manganite (CuMn$_2$O$_4$@C) nanoparticles, which method may circumvent the drawbacks such as, high cost, high environmental impact, and low yield, of methods known in the art.

SUMMARY

In an exemplary embodiment, a method of preparing nanoparticles of carbon-supported copper manganite (CuMn$_2$O$_4$) is described. The method includes preparing a first solution of a copper (II) salt and a manganese salt in a first polar organic solvent, where the molar ratio of copper (Cu):manganese (Mn) is from about 0.8:1 to about 1.2:1. The method further includes admixing a second solution of an organic ligand in a second polar organic solvent with the first solution to form a first mixture, and the second polar organic solvent is miscible with said first polar organic solvent, and hydrothermally heating the first mixture at a temperature of from about 100° C. to about 200° C. for a sufficient duration to form a solid metal-organic framework composite material, and calcining said metal-organic framework composite material at a temperature of from about 350° C. to about 600° C.

In some embodiments, the copper salt is selected from the group consisting of copper (II) sulfate (CuSO$_4$), copper (II) nitrate (Cu(NO$_3$)$_2$), copper (II) chloride (CuCl$_2$) and copper (II) acetate (Cu(CH$_3$COO)$_2$).

In some embodiments, the copper salt is copper (II) nitrate (Cu(NO$_3$)$_2$).

In some embodiments, the manganese salt is selected from the group consisting of manganese sulfate (MnSO$_4$), manganese nitrate (Mn(NO$_3$)$_2$), manganese chloride (MnCl$_2$) and manganese acetate (Mn(CH$_3$COO)$_2$).

In some embodiments, the manganese salt is manganese chloride (MnCl$_2$).

In some embodiments, the molar ratio of Cu:Mn in the first solution is from about 0.9:1 to about 1.1:1.

In some embodiments, the first polar organic solvent comprises at least one compound selected from the group consisting of dimethylformamide (DMF), diethylformamide (C$_5$H$_{11}$NO), acetonitrile (CH$_3$CN), water (H$_2$O), methanol (CH$_3$OH), ethanol (CH$_3$CH$_2$OH), isopropanol (C$_3$H$_8$O), 1-butanol (C$_4$H$_{10}$O) and acetone (C$_3$H$_6$O).

In some embodiments, the first polar organic solvent comprises dimethylformamide and ethanol.

In some embodiments, the second polar organic solvent comprises at least one compound selected from the group consisting of dimethylformamide, diethylformamide, acetonitrile, water, methanol, ethanol, isopropanol, 1-butanol and acetone.

In some embodiments, the second polar organic solvent consists of dimethylformamide.

In some embodiments, the organic ligand comprises at least one polycarboxylic acid.

In some embodiments, the organic ligand comprises at least one dicarboxylic acid selected from the group consisting of at least one dicarboxylic acid selected from the group consisting of ethanedioic acid, propanedioic acid, fumaric acid, benzene-1,4-dicarboxylic acid, benzene-1,3-dicarboxylic acid, benzene-1,2-dicarboxylic acid, 2,2'-bipyridine-5, 5'-dicarboxylic acid and 2,2'-bipyridine-4,4'-dicarboxylic acid.

In some embodiments, the organic ligand comprises at least one aromatic dicarboxylic acid selected from the group consisting of benzene-1,4-dicarboxylic acid, benzene-1,3-dicarboxylic acid, benzene-1,2-dicarboxylic acid, 2,2'-bipyridine-5,5'-dicarboxylic acid and 2,2'-bipyridine-4,4'-dicarboxylic acid.

In some embodiments, the organic ligand consists of benzene-1,4-dicarboxylic acid.

In some embodiments, the calcination temperature is from about 350° C. to about 450° C.

The present disclosure also describes the nanoparticles of carbon-supported copper manganite ($CuMn_2O_4$) obtained according to the method defined above, wherein: the copper manganite ($CuMn_2O_4$) of the nanoparticles has a crystalline spinel lattice which comprises copper in each of the $Cu^+$ and $Cu^{2+}$ oxidation states and comprises manganese in each of the $Mn^{3+}$ and $Mn^{4+}$ oxidation states; and, a fraction of the nanoparticles have a core-shell morphology in a which a shell of elemental carbon at least partially encapsulates a core nanoparticle of copper manganite ($CuMn_2O_4$). The present disclosure still further describes a method of dehydrogenating gaseous butan-2-ol ($C_4H_{10}O$) at a temperature of from about 200° C. to about 400° C. in the presence of nanoparticles of the carbon-supported copper manganite obtained according to the method as defined above, to form methyl ethyl ketone (MEK), where the gaseous butan-2-ol is carried in an inert gas.

In some embodiments, the dehydrogenation temperature is from about 250° C. to about 400° C.

In some embodiments, the inert gas consists essentially of nitrogen.

The foregoing general description of the illustrative embodiments and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
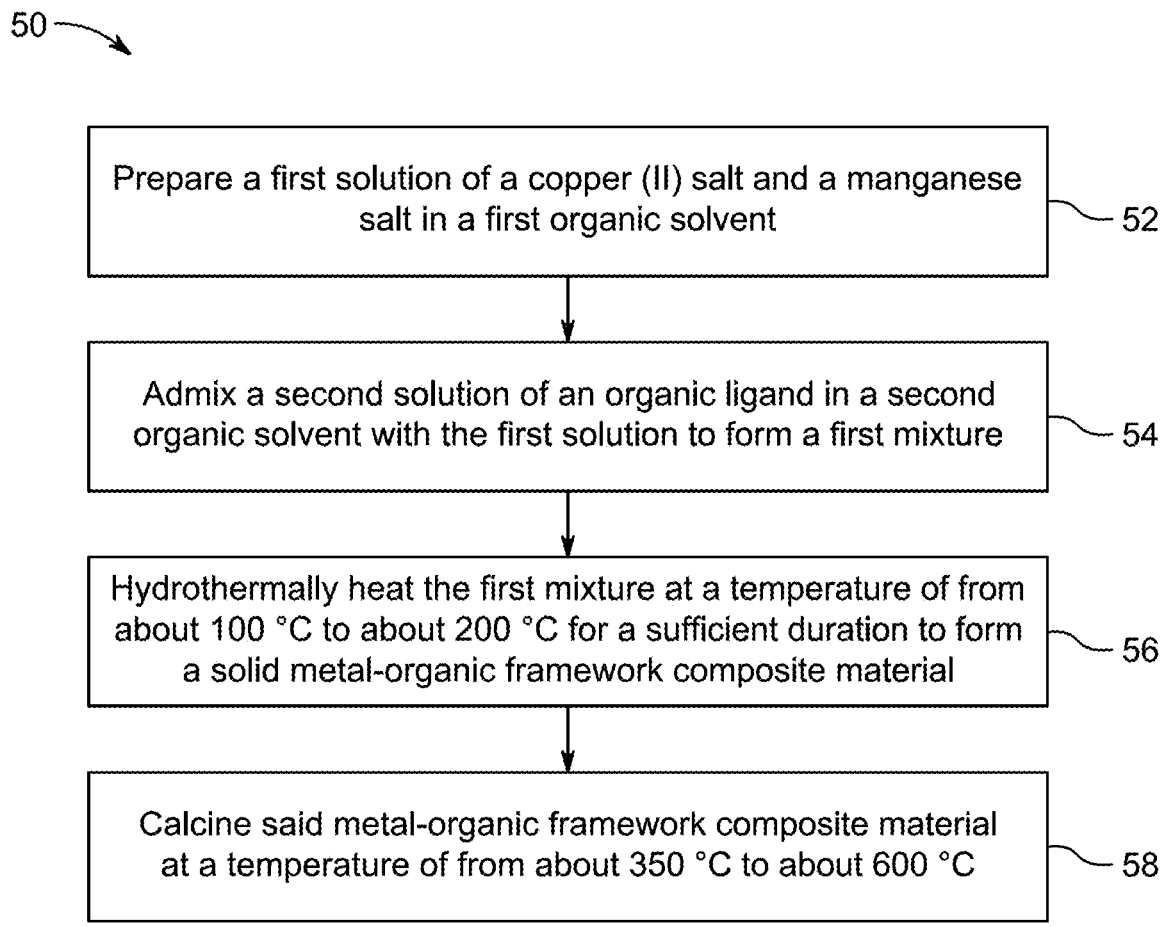
FIG. 1 is a flow chart depicting a method of preparing nanoparticles of carbon-supported copper manganite ($CuMn_2O_4$), according to certain embodiments.

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values there between.

The term 'fraction' as used herein refers to a numerical quantity which defines a part up to but not including 100 percent or the entirety of the thing in question.

When amounts, concentrations, dimensions and other parameters are expressed in the form of a range, a preferable range, an upper limit value, a lower limit value or preferable upper and limit values, it should be understood that any ranges obtainable by combining any upper limit or preferable value with any lower limit or preferable value are also specifically disclosed, irrespective of whether the obtained ranges are clearly mentioned in the context.

As used herein, the term 'particle' refers to a small object that acts as a whole unit with regard to its transport and properties.

Unless otherwise stated, the term "particle size" refers to the largest axis of the particle. In the case of a generally spherical particle, the largest axis is the diameter.

The term "median volume particle size" (Dv50), as used herein, refers to a particle size corresponding to 50% of the volume of the sampled particles being greater than and 50% of the volume of the sampled particles being smaller than the recited Dv50 value. Particle size is determined herein by Scanning Electron Microscopy (SEM).

As used herein, 'nanoparticles'-sometimes contracted herein to NPs-refers to particles having a particle size of 1 nanometer (nm) to 1000 nm. The nanoparticles of $CuMn_2O_4$@C may possess various morphological forms. It is envisaged, for example, that nanoparticles of $CuMn_2O_4$@C that are fibrous, acicular, spherical, ellipsoidal, cylindrical, bead-like, cubic or platelet-like may be present alone or in combination. Moreover, it is envisaged that agglomerates of nanoparticles having the same or different morphologies may be present in the nanocomposite.

By the term 'substantially spherical' is meant a shape which includes spherical as well as other distorted shapes, such as ovate, ovoid, or ellipsoid, but which in any event has two orthogonal cross sections which are closed shapes having no substantially straight sides.

The term 'at least partially encapsulated with elemental carbon' is used hereto to indicate that, as determined by scanning electron micrograph, at least about 10% of the surface area of the particle in question is in contact with elemental carbon. In exemplary embodiments, at least about 20%, at least about 40%, at least about 60% or at least about 80% of the surface area of the particle in question is in contact with elemental carbon, or the particle is completely encased in a carbon shell with no surface of the particle exposed.

The term "miscible" as used herein references the ability of two or more solvents to form a single liquid phase when mixed together.

The term "polar solvent" as used herein refers to a solvent having a dielectric constant (8) of more than 5 as measured at 25° C. The determination of dielectric constant (8) is known in the art: the use of measured voltages across parallel plate capacitors in such determinations may be mentioned. The term "polar solvent" may encompass both aprotic and protic solvents, wherein protic solvents are those solvents which are capable of yielding or accepting a proton and aprotic solvents are those solvents that do not yield or accept a proton.

As used herein, the term "organic ligand" refers to a molecule that contains one or more donor atoms, such as oxygen, nitrogen, or sulfur, which are capable of coordinating to a central metal ion to form a metal-ligand complex. Organic ligands typically have functional groups such as carboxylates, amines, phosphines, or pyridines, and they play a crucial role in stabilizing metal ions, facilitating chemical reactions, and modulating the reactivity of metal centers. Examples of organic ligands include ethylenediamine, ethylenediaminetetraacetic acid (EDTA), bipyridyl, phthalate, and various polycarboxylic acids, among others. Organic ligands are commonly used in coordination chemistry, catalysis, and materials science.

As used herein, the term "metal-organic framework" (MOF) refers to a class of materials composed of metal ions or metal clusters coordinated to organic ligands, forming a three-dimensional network structure. These frameworks are characterized by their high surface area, tunable porosity, and structural versatility. MOFs are typically constructed by linking metal centers, such as copper or manganese, with organic ligands, such as carboxylates, phosphonates, or bipyridines. The resulting structures can be highly porous, making them useful for applications in gas storage, catalysis, separation, drug delivery, and sensing. MOFs are known for their ability to absorb and store various molecules due to their large surface area and flexible structures.

As used herein with respect to X-ray diffraction analysis, "JCPDS" denotes the Joint Committee on Powder Diffraction Standards.

As used herein, the term "biofuel" refers to a type of fuel that is derived from renewable biological sources, such as plant or animal matter. Biofuels are typically used as alternatives to conventional fossil fuels and include substances like ethanol, biodiesel, biogas, and bioethanol. These fuels are produced through processes such as fermentation, transesterification, or anaerobic digestion and can be used for transportation, electricity generation, and heating. Biofuels are considered more sustainable than fossil fuels because they are renewable, reduce greenhouse gas emissions, and help decrease dependence on non-renewable energy sources. Examples of biofuels include ethanol produced from corn or sugarcane, biodiesel derived from vegetable oils or animal fats, and methane from organic waste.

The term 'hydrothermally heating' as used herein refers to a method of heating which utilizes $H_2O$ as a heat transfer medium.

As used herein, the term 'calcination' refers to a thermal treatment process which is conducted in the absence of, or under a restricted supply of ambient oxygen. This is performed to remove impurities or volatile substances and/or to induce thermal decomposition or a change in the thermally treated material.

As used herein, the term 'Gas Hourly Space Velocity' or 'GHSV' means the unit volume of gas at the stated temperature and pressure passing over one unit weight of packed catalyst per hour.

The term 'selectivity' as used herein refers to the selectivity of the dehydrogenation reaction to form the desired product (e.g., methyl ethyl ketone) as opposed to undesired product(s). The percentage selectivity may be calculated according to the following equation: % Selectivity=100*(D/T), wherein D is the number of moles of the desired product obtained and T is the total number of moles of product(s) obtained.

As used herein, the term "inert gas" refers to a gas that is chemically non-reactive under the conditions of use. These gases have a stable electron configuration and do not readily form compounds with other elements or molecules. Inert gases are often used in various processes to create an environment that prevents unwanted chemical reactions, such as oxidation or combustion. Common examples of inert gases include helium, argon, neon, krypton, xenon, and nitrogen.

Aspects of this disclosure are directed to a method of preparing carbon-supported copper manganite ($CuMn_2O_4$) and the generation of methyl ethyl ketone (MEK) biofuel. MEK biofuel has potential to provide a renewable, high-energy-density alternative to conventional fuels, contributing to reduced dependence on fossil fuels and lower environmental impact.

FIG. 1 illustrates a schematic flow chart of a method 50 of a method of preparing nanoparticles of carbon-supported copper manganite ($CuMn_2O_4$) is described. The order in which the method 50 is described is not intended to be construed as a limitation, and any number of the described method steps can be combined to implement the method 50. Additionally, individual steps may be removed or skipped from the method 50 without departing from the spirit and scope of the present disclosure.

At step 52, the method 50 includes preparing a first solution of a copper (II) salt and a manganese salt in a first polar organic solvent. In some embodiments, the copper salt may be selected from the group consisting of copper (II) sulfate ($CuSO_4$), copper (II) nitrate ($Cu(NO_3)_2$), copper (II) chloride ($CuCl_2$), and copper (II) acetate ($Cu(CH_3COO)_2$), copper (II) bromide ($CuBr_2$), copper (II) iodide (CuI2), copper (II) oxide (CuO), copper (II) acetate monohydrate ($Cu(CH_3COO)_2 \cdot H_2O$), copper (II) carbonate ($CuCO_3$), copper (II) carbonate hydroxide ($Cu_2(CO_3)(OH)_2$), copper (II) formate ($Cu(HCOO)_2$), copper (II) oxalate ($CuC_2O_4$), copper (II) phosphate ($Cu_3(PO_4)_2$), copper (II) sulfate pentahydrate ($CuSO_4 \cdot 5H_2O$), copper (II) tartrate ($Cu(C_4H_4O_6)$), copper (II) malate ($Cu(C_4H_6O_5)$), copper (II) citrate ($Cu_3$ ($C_6H_5O_7)_2$), copper (II) lactate ($Cu(C_3H_5O_3)_2$), copper (II) gluconate ($Cu(C_6H_{11}O_7)_2$), copper (II) benzoate ($Cu(C_7H_6O_2)_2$), copper (II) salicylate ($Cu(C_7H_6O_3)$), copper (II) sulfate heptahydrate ($CuSO_4 \cdot 7H_2O$), copper (II) hexahydrate ($CuSO_4 \cdot 6H_2O$), copper (II) nitrate trihydrate ($Cu(NO_3)_2 \cdot 3H_2O$), copper (II) perchlorate ($Cu(ClO_4)_2$), and copper (II) stearate ($Cu(C_{18}H_{35}O_2)_2$). The copper salt may, in exemplary embodiments, be selected from the group consisting of copper (II) sulfate ($CuSO_4$), copper (II) nitrate ($Cu(NO_3)_2$), copper (II) chloride ($CuCl_2$) and copper (II) acetate ($Cu(CH_3COO)_2$). In a preferred embodiment, the copper salt is copper (II) nitrate ($Cu(NO_3)_2$).

In some embodiments, the manganese salt may include, but is not limited to, manganese (II) oxide (MnO), manganese (III) chloride ($MnCl_3$), manganese (IV) oxide ($MnO_2$), manganese (II) carbonate ($MnCO_3$), manganese (II) formate ($Mn(HCOO)_2$), manganese (II) phosphate ($Mn_3(PO_4)_2$), manganese (II) acetate monohydrate ($Mn(CH_3COO)_2 \cdot H_2O$), manganese (II) bromide ($MnBr_2$), manganese (II) iodide ($MnI_2$), manganese (III) acetate ($Mn(CH_3COO)_3$), manganese (II) sulfate monohydrate ($MnSO_4 \cdot H_2O$), manganese (II) pyrophosphate ($Mn_2P_2O_7$), manganese (II) gluconate ($Mn(C_6H_{11}O_7)_2$), manganese (II) lactate ($Mn(C_3H_5O_3)_2$), manganese (II) tartrate ($Mn(C_4H_4O_6)$), manganese (II) malate ($Mn(C_4H_6O_5)$), manganese (III) formate ($Mn(HCOO)_3$), manganese (II) citraconate ($Mn(C_5H_6O_4)$), and manganese (II) salicylate ($Mn(C_7H_6O_3)$). The manganese salt may, in exemplary embodiments, be selected from the group consisting of manganese sulfate ($MnSO_4$), manganese nitrate ($Mn(NO_3)_2$), manganese chloride ($MnCl_2$) and manganese acetate ($Mn(CH_3COO)_2$). In a preferred embodiment, the manganese salt is manganese chloride ($MnCl_2$).

In some embodiments, the ratio of the number of moles of copper (Cu) to the number of moles of manganese-hereinafter the molar ratio of Cu:Mn—in the first solution may range from about 0.8:1 to about 1.2:1, for example from about 0.9:1 to about 1.1:1 or from about 0.95:1 to about 1.05:1. In a preferred embodiment, the molar ratio of Cu:Mn in the first solution is about 1:1.

Typically the first organic solvent is a polar solvent having a boiling point of at least about 20° C., for instance at least about 30° C. or at least about 40° C., as measured at 1 atmosphere pressure (1.01325 Bar). Examples of polar organic compounds, which may be used alone or in combination as the first solvent, include: $C_1$-$C_8$ alkanols, such as methanol, ethanol, n-propanol, isopropanol, n-butanol, sec-butanol and isobutanol; acetonitrile; N,N-di($C_1$-$C_4$)alkylacrylamides, such as N,N-dimethylformamide (DMF), N,N-diethylformamide and N,N-dimethylacetamide (DMAc); hexamethylphosphoramide; N-methylpyrrolidone; pyridine; esters, such as ($C_1$-$C_8$)alkyl acetates, ethoxydiglycol acetate, dimethyl glutarate, dimethyl maleate, dipropyl oxalate, ethyl lactate, benzyl benzoate, butyloctyl benzoate and ethylhexyl benzoate; ketones, such as acetone, ethyl ketone, methyl ethyl ketone (2-butanone) and methyl isobutyl ketone; ethers, such as tetrahydrofuran (THF), 2-methyltetrahydrofuran (2-MeTHF) and 1,2-dimethoxyethane; 1,3-dioxolane; dimethylsulfoxide (DMSO); and, dichloromethane (DCM).

In an exemplary embodiment, the first polar organic solvent comprises at least one compound selected from the group consisting of dimethylformamide, diethylformamide, acetonitrile, methanol, ethanol, isopropanol, 1-butanol and acetone. In a further exemplary embodiment, the first polar organic solvent comprises dimethylformamide and ethanol.

At step 54, the method 50 includes admixing a second solution of an organic ligand in a second polar organic solvent with the first solution to form a first mixture. The second polar organic solvent is miscible with said first organic solvent.

Typically the second polar organic solvent is a polar solvent having a boiling point of at least about 20° C., for instance at least about 30° C. or at least about 40° C., as measured at 1 atmosphere pressure (1.01325 Bar). The exemplary polar organic compounds mentioned herein above with respect to the first organic solvent may be used alone or in combination in the second organic solvent. In an exemplary embodiment, however, the second polar organic solvent comprises at least one compound selected from the group consisting of dimethylformamide, diethylformamide, acetonitrile, methanol, ethanol, isopropanol, 1-butanol and acetone. In a further exemplary embodiment, the second polar organic solvent comprises or consists of dimethylformamide.

In some embodiments, the organic ligand includes at least one polycarboxylic acid. The organic ligand includes at least one dicarboxylic acid selected from ethanedioic acid, propanedioic acid, fumaric acid, benzene-1,4-dicarboxylic acid, benzene-1,3-dicarboxylic acid, benzene-1,2-dicarboxylic acid, 2,2'-bipyridine-5,5'-dicarboxylic acid and 2,2'-bipyridine-4,4'-dicarboxylic acid. In some embodiments, the organic ligand includes at least one aromatic dicarboxylic acid selected from benzene-1,4-dicarboxylic acid, benzene-1,3-dicarboxylic acid, benzene-1,2-dicarboxylic acid, 2,2'-bipyridine-5,5'-dicarboxylic acid and 2,2'-bipyridine-4,4'-dicarboxylic acid. In a preferred embodiment, the organic ligand includes benzene-1,4-dicarboxylic acid.

At step 56, the method 50 includes hydrothermally heating the first mixture at a temperature of from about 100 to about 200° C. for a sufficient duration to form a solid metal-organic framework composite material. In some embodiments, the first mixture is hydrothermally heated at a temperature ranging from about 100° C. to about 180° C., for example from about 100° C. to about 160° C., from about 100° C. to about 140° C., or from about 110° C. to about 130° C. In a preferred embodiment, the first mixture is hydrothermally heated at a temperature of 120° C.

In some embodiments, the first mixture is hydrothermally heated at the aforementioned temperatures for a duration of from about 10 hours to about 28 hours, for example about 12 hours, about 14 hours, about 16 hours, about 18 hours, about 20 hours, about 22, about 24 hours, about 26 hours, or about 28 hours. In an exemplary embodiment, the first mixture is hydrothermally heated at about 120° C. for 24 hours to form a solid metal-organic framework composite material.

At step 58, the method 50 includes calcining said metal-organic framework composite material at a temperature of from about 350° C. to about 600° C. In some embodiments, the calcination temperature may range from about 350° C. to about 550° C., for example from about 350° C. to about 500° C., or preferably from about 350° C. to about 450° C.

The calcination step yields particulates of carbon-supported copper manganite. Typically, the particulates may have a median volume particle size (Dv50), as determined by Scanning Electron Microscopy (SEM), of from about 10 to about 100 nm, for example of from about 10 to about 75 nm or from about 10 to about 50 nm. It is not however precluded in the present method, that the nanoparticles directly obtained from the calcination step may be subjected to at least one of comminution, homogenization or classification in order to moderate the particle size distribution thereof.

As may be determined by powder X-ray diffraction, the obtained nanoparticles of copper-supported copper manganite comprise the $CuMnO_4$ spinel phase, wherein copper cations occupy tetrahedral sites and manganese cations occupy octahedral sites within the crystal lattice. The cubic spinel structure is predominant in some embodiments but it is not precluded that tetragonal distortion of the crystal lattice may be identifiable.

Figure 7A:
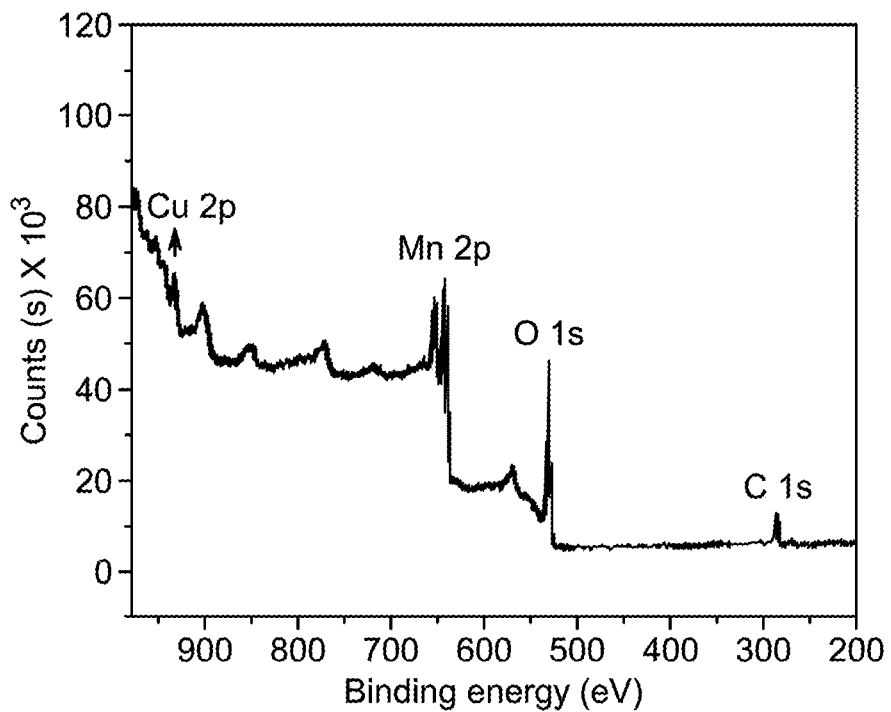
FIG. 7A shows a high-resolution x-ray photoelectron spectroscopy (XPS) survey of $CuMn_2O_4$@C, according to certain embodiments.
Figure 7B:
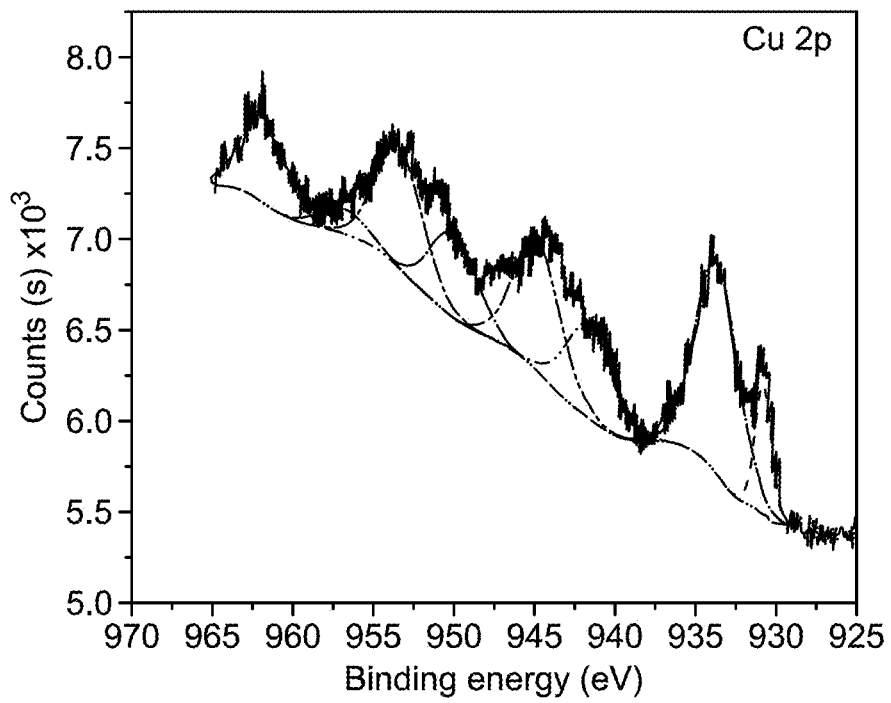
FIG. 7B is a high-resolution XPS spectrum of Cu 2p of $CuMn_2O_4$@C, according to certain embodiments.

As determined by X-ray photoelectron spectroscopy—of which FIG. 7B appended hereto provides an illustrative determination—the Cu ions present in the $CuMn_2O_4$ spinel exist in both of the $Cu^+$ and $Cu^{2+}$ oxidation states. More particularly: a major first fraction ($f^{1,t}$) of the tetrahedral sites within the $CuMn_2O_4$ crystal lattice may be occupied by $Cu^{2+}$ ions; and, a minor second fraction ($f^{2,t}$) of the tetrahedral sites within the $CuMn_2O_4$ lattice may be occupied by $Cu^+$ ions. For example: the first major fraction ($f^{1,t}$; $Cu^{2+}$) may constitute from about 55 to about 95%, such as from about 60 to about 90% or about 70 to about 90% of the total number of tetrahedral sites within the $CuMn_2O_4$ crystal lattice; and, the second minor fraction ($f^{2,t}$; $Cu^+$) may constitute from about 5 to about 45%, such as from about 10 to about 40% or from about 10 to about 30% of the total number of tetrahedral sites within the $CuMn_2O_4$ crystal lattice.

Further, the Mn ions present in the $CuMn_2O_4$ spinel of the supported nanocomposite exist in both of the $Mn^{3+}$ and $Mn^{4+}$ oxidation states, as determined by X-ray photoelectron spectroscopy. More particularly: a major first fraction ($f^{1,o}$) of the octahedral sites within the $CuMn_2O_4$ crystal lattice may be occupied by $Mn^{3+}$ ions; and, a minor second fraction ($f^{2,o}$) of the octahedral sites within the $CuMn_2O_4$ lattice may be occupied by $Mn^{4+}$ ions. For example: the first major fraction ($f^{1,o}$; $Mn^{3+}$) may constitute from about 55 to about 95%, such as about 60 to about 90% or from about 70 to about 90% of the total number of octahedral sites within the $CuMn_2O_4$ crystal lattice; and, the second minor fraction ($f^{2,o}$; $Mn^{4+}$) may constitute from about 5 to about 45%, such as from about 10 to about 40% or from about 10 to about 30% of the total number of octahedral sites within the $CuMn_2O_4$ crystal lattice.

Figure 7C:
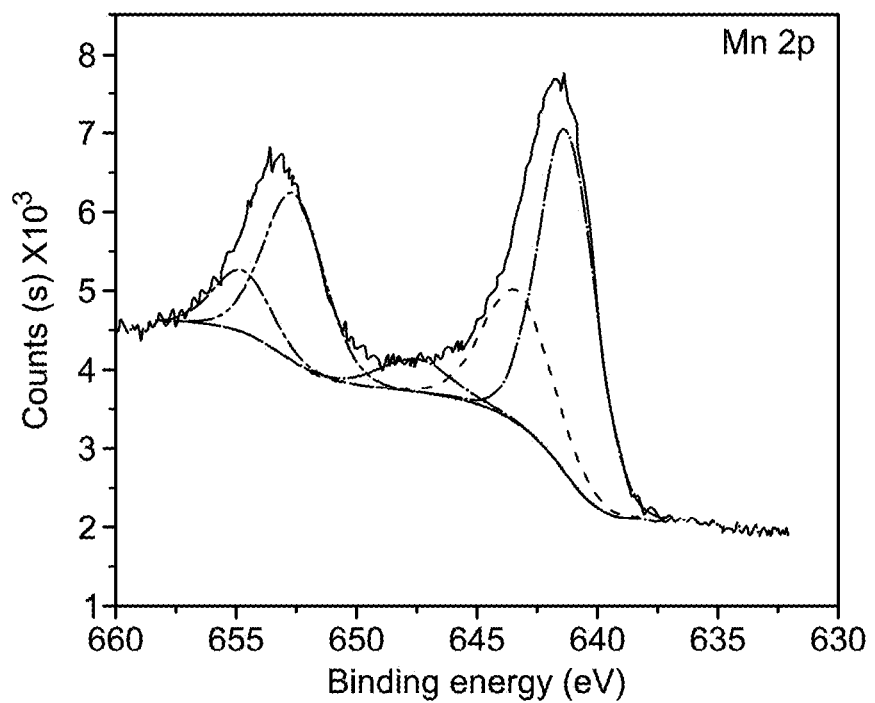
FIG. 7C is a high-resolution XPS spectrum of Mn 2p of $CuMn_2O_4$@C, according to certain embodiments.
Figure 7D:
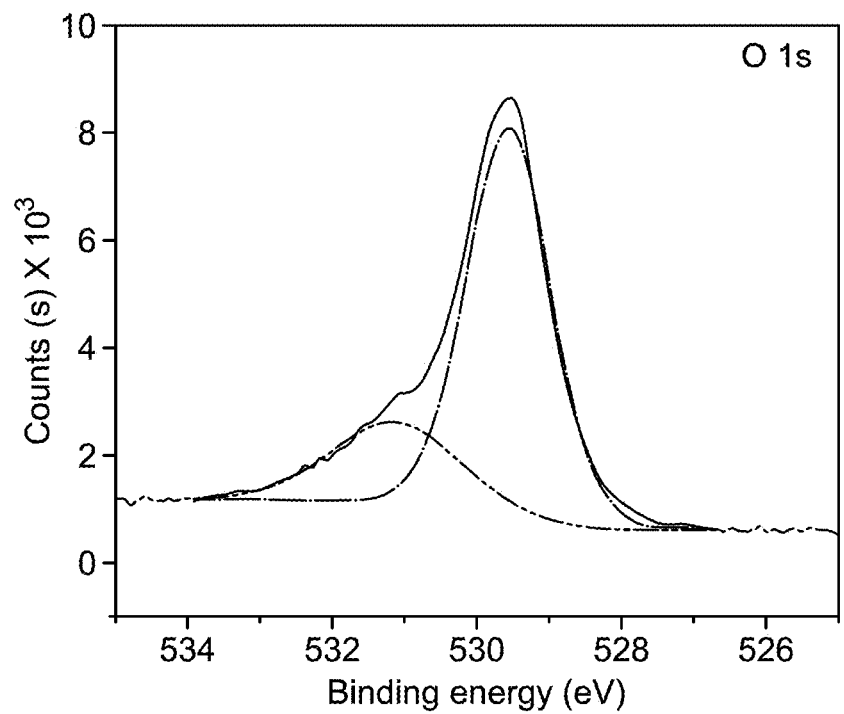
FIG. 7D is a high-resolution XPS spectrum of O 1S of $CuMn_2O_4$@C, according to certain embodiments.

As may be evidenced by O 1s X-ray photoelectron spectroscopy—of which FIG. 7D appended hereto provides an example—the carbon-supported $CuMn_2O_4$ nanocomposite may comprise chemisorbed oxygen. For example, the molar ratio of chemisorbed oxygen to oxygen bound in the $CuMnO_4$ lattice of the carbon-supported $CuMn_2O_4$ nanocomposite may be from about 1:2 to about 1:20, such as from about 1:2 to about 1:15 or about 1:2 to about 1:10. Without intention to be bound by theory, the different oxidation states of the Cu and Mn of the $CuMn_2O_4$ spinel may facilitate the surface adsorption of oxygen molecules.

Figure 7E:
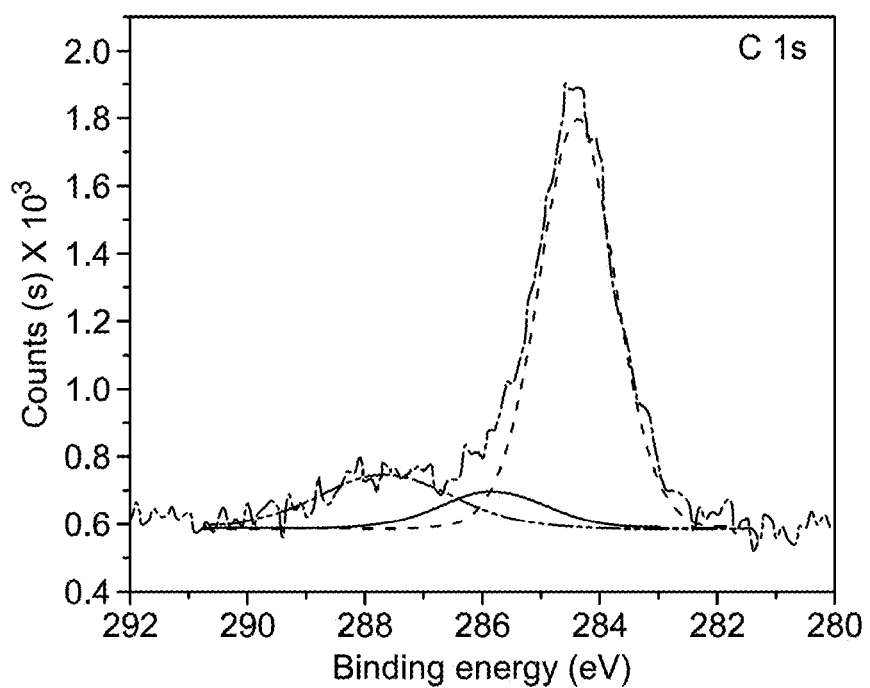
FIG. 7E is a high-resolution XPS spectrum of C 1S of $CuMn_2O_4$@C, according to certain embodiments.

As may be further determined by X-ray photoelectron spectroscopy (XPS)—of which FIG. 7E appended hereto provides an illustrative determination—the carbon of the nanoparticles does not significantly chemically bond with the oxygen atoms of the $CuMnO_4$ structure. The carbon Is spectrum confirms the C—C bond as being predominant, indicating that elemental carbon acts as a physical support for the copper manganite. A fraction of the nanoparticles have a core-shell morphology in a which a shell of elemental carbon at least partially encapsulates a core nanoparticle of copper manganite ($CuMnO_4$). In a particular embodiment, a fraction of the nanoparticles have a core-shell morphology in which a shell of elemental carbon at least partially encapsulates a core of a substantially spherical nanoparticle of copper manganite.

The present disclosure also provides for the use of the carbon-supported copper manganite ($CuMn_2O_4$) nanoparticles for the generation of methyl ethyl ketone (MEK). More particularly, the present disclosure provides a method of preparing methyl ethyl ketone (MEK) comprising dehydrogenating gaseous butan-2-ol at a temperature of from about 200 to about 400° C. in the presence of nanoparticles of carbon-supported copper manganite as described herein above, wherein the gaseous butan-2-ol is carried in an inert gas.

The nanoparticles of carbon-supported copper manganite may conventionally be disposed in a fixed reactor bed. Gaseous butan-2-ol, carried by the inert gas, contacts the nanoparticles at the dehydrogenation temperature. The method is desirably performed semi-continuously or continuously such that an input stream of the carrier gas bearing butan-2-ol is passed over a fixed reactor bed comprising particles of carbon-supported copper manganite: a gaseous output stream comprising methyl ethyl ketone is then collected. The fixed reactor bed may be disposed in an appropriate chamber for which the temperature and pressure conditions of at least the gaseous input stream, the reactor bed and the gaseous output stream may be regulated.

There is no particular intention to limit the source of the butan-2-ol (sec-butanol, sec-butyl alcohol; $C_4H_{10}O$) to be dehydrogenated in the described method. For example, the butan-2-ol may be obtained from the indirect hydration of n-butene, derivable from a $C_4$-fossil stream. Alternatively or additionally, at least a fraction of the butan-2-ol may be derived from non-fossil sources, of which illustrative mention may be made of: the generation of butan-2-ol by the microbial fermentation described in US2008274525A1, the disclosure of which is included herein in its entirety; the selective production of butan-2-ol from α-valerolactone derivable from a lignocellulosic feedstock as described in U.S. Pat. No. 10,865,170 B2, the disclosure of which is included herein in its entirety; the separation of butan-2-ol from the products of the acetone-butanol-ethanol (ABE) fermentation of sugar, glycerol, lignocellulosic feedstocks or algal feedstocks using *Clostridium* species; the production of butan-2-ol from the microbial consumption of meso-2,3-butanediol derivable from mixed acid fermentation; and, the production of butan-2-ol by aldol condensation of acetaldehyde followed by hydrogenation, which acetaldehyde may be derived from bio-ethanol.

Independently of its source, the butan-2-ol is combined in gaseous form with the inert carrier gas. This may be effected by first vaporizing the butan-2-ol and then combining the vapor with the inert carrier gas. In the alternative, butan-2-ol may be heated above its boiling point in the presence of the inert carrier. The step of vaporizing the butan-2-ol and combining it with the inert carrier gas may be conducted at temperature below the subsequent catalyzed dehydrogenation temperature: the first formed combination may then be subjected to further heating prior to contacting the nanoparticles of carbon-supported copper manganite.

In some embodiments, the inert gas used as carrier may be selected from the group consisting of argon, helium, neon, krypton, xenon, radon, hydrogen, methane, carbon dioxide, sulfur hexafluoride and mixtures thereof. For instance, the inert gas may be mixture of hydrogen and nitrogen. In a preferred embodiment, the inert gas consists essentially of nitrogen.

The ratio by weight of butan-2-ol to inert gas in the gaseous feed which contacts the nanoparticles of carbon-supported copper manganite is typically from about 1:1 to 1:10, for example from about 1:2 to about 1:10 or from about 1:3 to about 1:10. Independently of, or additional to conformity to the stated ratios by weight in the gaseous feed, the dehydrogenation may be exemplified by a gas hourly space velocity of from about 100 to about 20000 hr$^{-1}$, for example from about 1000 to about 10000 hr$^{-1}$ or from about 2000 to 10000 hr$^{-1}$.

Referring back, the dehydrogenation temperature at which the gaseous 2-butanol contacts the nanoparticles of carbon-supported copper manganite is from about 200° C. to about 400° C. For example, the dehydrogenation temperature may be from about 225 to about 400° C. or from about 250 to about 400° C. Independently of the temperature, the dehydrogenation may be performed at a pressure of from about 0.1 to about 1 MPa, for example from about 0.1 to about 0.8 MPa or from 0.1 to 0.5 MPa.

The dehydrogenation of butan-2-ol over the carbon-supported copper manganite nanoparticles yields methyl ethyl ketone and, at a reaction selectivity of less than 100%, co-products such as but-1-ene, cis-but-2-ene, trans-but-2-ene and $H_2O$. The products collected from the dehydrogenation reaction may further comprise unreacted butan-2-ol.

The methyl ethyl ketone may be separated from the co-products and unreacted butan-2-ol. Exemplary methods of separation include the condensation of the reaction products and subsequently either azeotropic distillation of the condensate to isolate methyl ethyl ketone or liquid-liquid extraction of methyl ethyl ketone from the condensate. The step of condensation may be performed in a heat-exchanger whereby the heat released may be used to vaporize butan-2-ol provided to the dehydrogenation reaction.

As compared to carbon-supported copper (II) oxide (CuO) and carbon-supported manganese (III) oxide prepared in an analogous manner, the nanoparticles of carbon-supported $CuMn_2O_4$ of the present disclosure provide enhanced catalytic activity and selectivity for the dehydrogenation of butan-2-ol to methyl ethyl ketone. Without intention to be bound by theory, the existence of both copper and manganese in more than one oxidation state in the $CuMn_2O_4$ crystalline spinel lattice may provide for favorable redox coupling between the Cu and Mn, facilitating electron transfer during the catalytic dehydrogenation. Further, the presence of copper in the lattice of manganese oxide may also serve to increase the mobility of lattice oxygen which, in addition to surface chemisorbed oxygen, would become available for oxidation reactions.

Examples

The following examples demonstrate a method of preparing nanoparticles of carbon-supported copper manganite ($CuMn_2O_4$@C) via an intermediate metal-organic framework. The examples are provided solely for illustration and are not to be construed as limitations of the present disclosure, as many variations thereof are possible without departing from the spirit and scope of the present disclosure.

Example 1: Fabrication of Carbon-Supported Copper Manganite $CuMn_2O_4$@C Nano Catalysts A one-step solvothermal approach was used to create the Cu—Mn-benzene-1,4-dicarboxylate (BDC) Metal Organic Framework (MOF). (Accordingly, 80 mL of dimethylformamide (DMF) was used to dissolve 1.7 g of $MnCl_2 \cdot 4H_2O$, 1.0 g $Cu(NO_3)_2 \cdot 3H_2O$ and 1.9 g of benzene-1,4-dicarboxylate (BDC) by stirring continuously for 40 minutes. 20 mL of methanol was then added and the mixture was stirred again for 10 minutes. The reaction mixture was transferred to a 150 mL stainless-steel autoclave lined with Teflon and then heated for 24 hours at 120° C. Centrifugation (10,000 rpm, 30 minutes) was used to collect the synthesized Cu—Mn-BDC product (MOF), which was subsequently cleaned three times with methanol. The product was dried for 24 hours at 80° C. in an oven and finally calcined at 400° C. for 3 hours to form the carbon-supported copper manganite ($CuMn_2O_4$@C). The pure carbon-supported oxides, CuO@C and $Mn_2O_3$@C, were prepared by the same abovementioned procedures for the purposes of comparison to the title composite.

Example 2: Generation of Methyl Ethyl Ketone (MEK)

Figure 2:
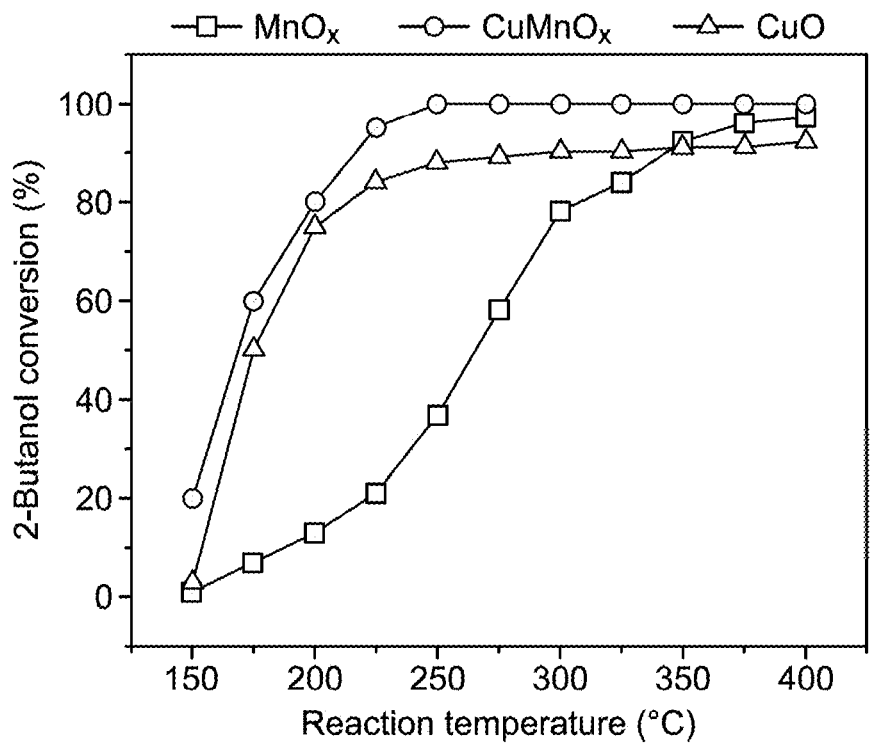
FIG. 2 is a graph depicting catalytic dehydrogenation of butan-2-ol into methyl ethyl ketone (MEK) over pure carbon-supported copper oxide (CuO@C), pure carbon-supported manganese (III) oxide ($Mn_2O_3$@C), and carbon-supported copper manganite ($CuMn_2O_4$@C) catalysts, calcined at 400° C., according to certain embodiments.
Figure 3:
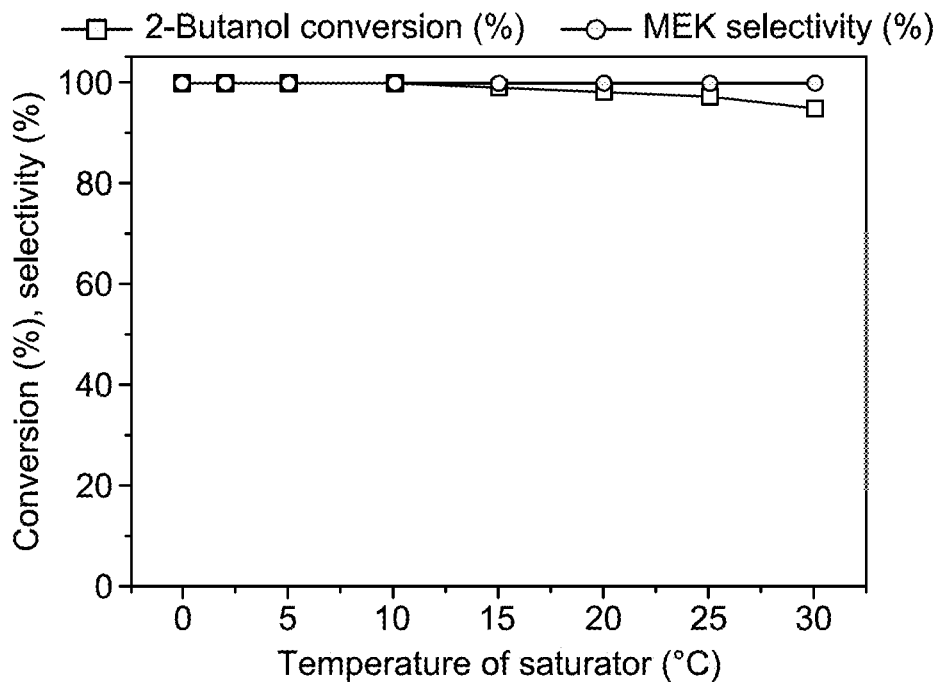
FIG. 3 is a graph depicting an effect of varying percentage (%) concentrations of butan-2-ol reactant on a dehydrogenation performance of butan-2-ol over a $CuMn_2O_4$@C catalyst, calcined at 400° C., with a dehydrogenation temperature of 250° C., according to certain embodiments.
Figure 4:
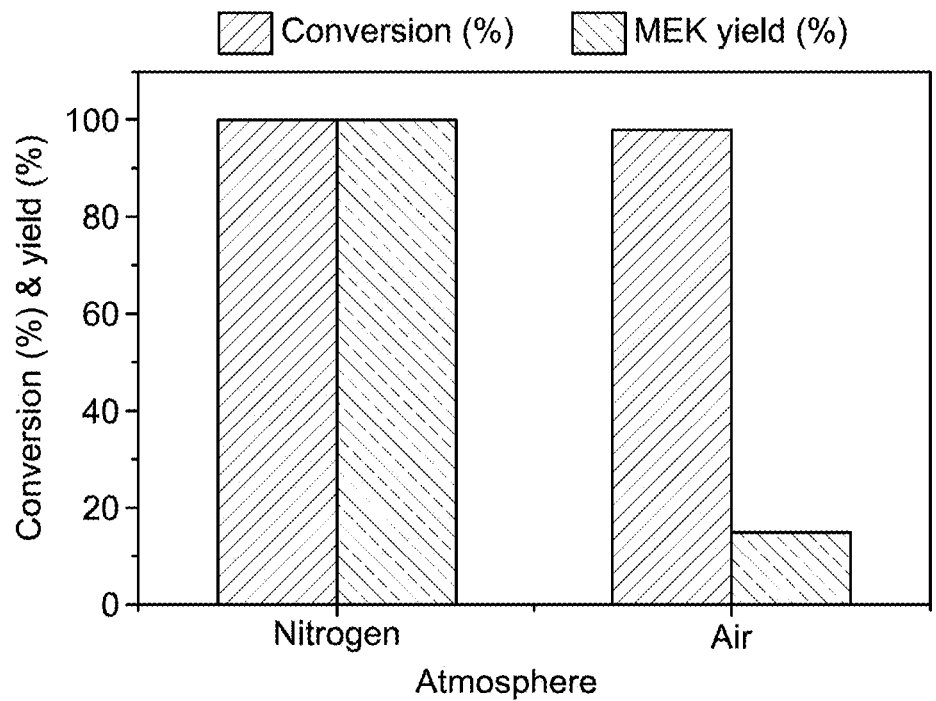
FIG. 4 is a graph depicting an effect of atmosphere type on catalytic dehydrogenation of butan-2-ol over the $CuMn_2O_4$@C catalyst, calcined at 400° C. with a dehydrogenation temperature of 250° C., according to certain embodiments.
Figure 5:
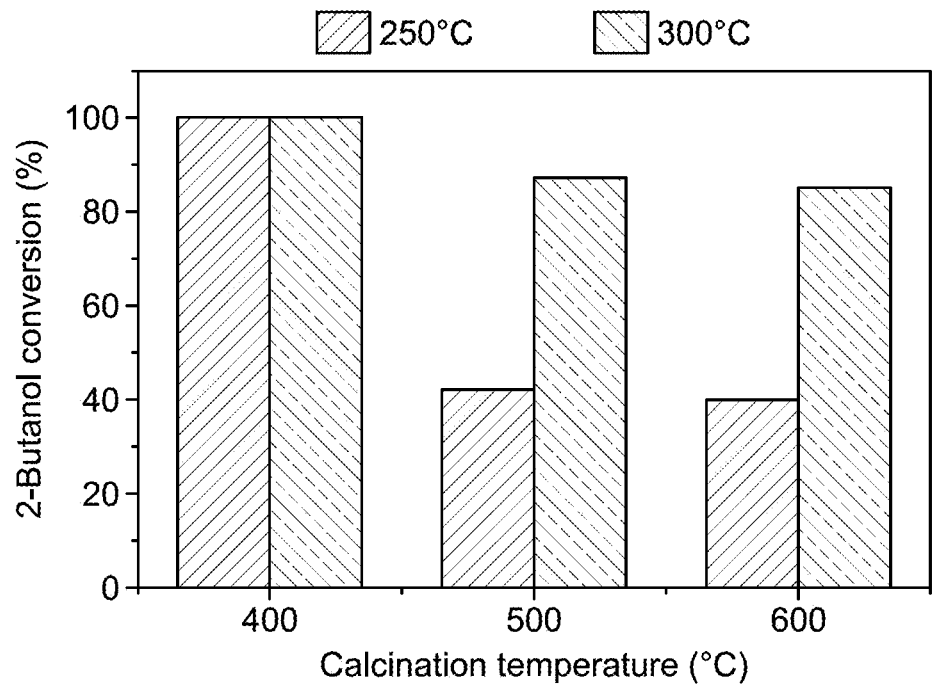
FIG. 5 illustrates an effect of calcination temperature of the $CuMn_2O_4$@C catalyst on the catalytic dehydrogenation of butan-2-ol at dehydrogenation temperatures of from 250° C. and 300° C., with a catalyst weight of 0.051 grams and at a gas flow rate of 100 ml per minute, according to certain embodiments.

According to the present disclosure, $CuMn_2O_4$@C was fabricated in accordance with Example 1 as a catalyst with high activity and selectivity to produce MEK. FIG. 2 depicts the results of butan-2-ol dehydrogenation in a temperature range of about 150° C. to 400° C., over pure carbon-supported copper oxide (CuO@C), pure carbon-supported manganese (III) oxide ($Mn_2O_3$@C), and $CuMn_2O_4$@C. The results indicated a synergistic effect where $CuMn_2O_4$@C catalyst exhibits activity higher than CuO@C and $Mn_2O_3$@C. Further, a complete conversion of butan-2-ol to MEK, with a selectivity of 100%, was obtained at a dehydrogenation temperature of about 250° C., as shown in FIG. 3. Furthermore, the impact of temperature of saturator (as an indicator to the percentage by weight of 2-butanol in the reacting stream), the calcination temperature and type of gas atmosphere, on the catalytic dehydrogenation of butan-2-ol over $CuMn_2O_4$@C was evaluated, as shown in FIG. 4 and FIG. 5.

Figure 6:
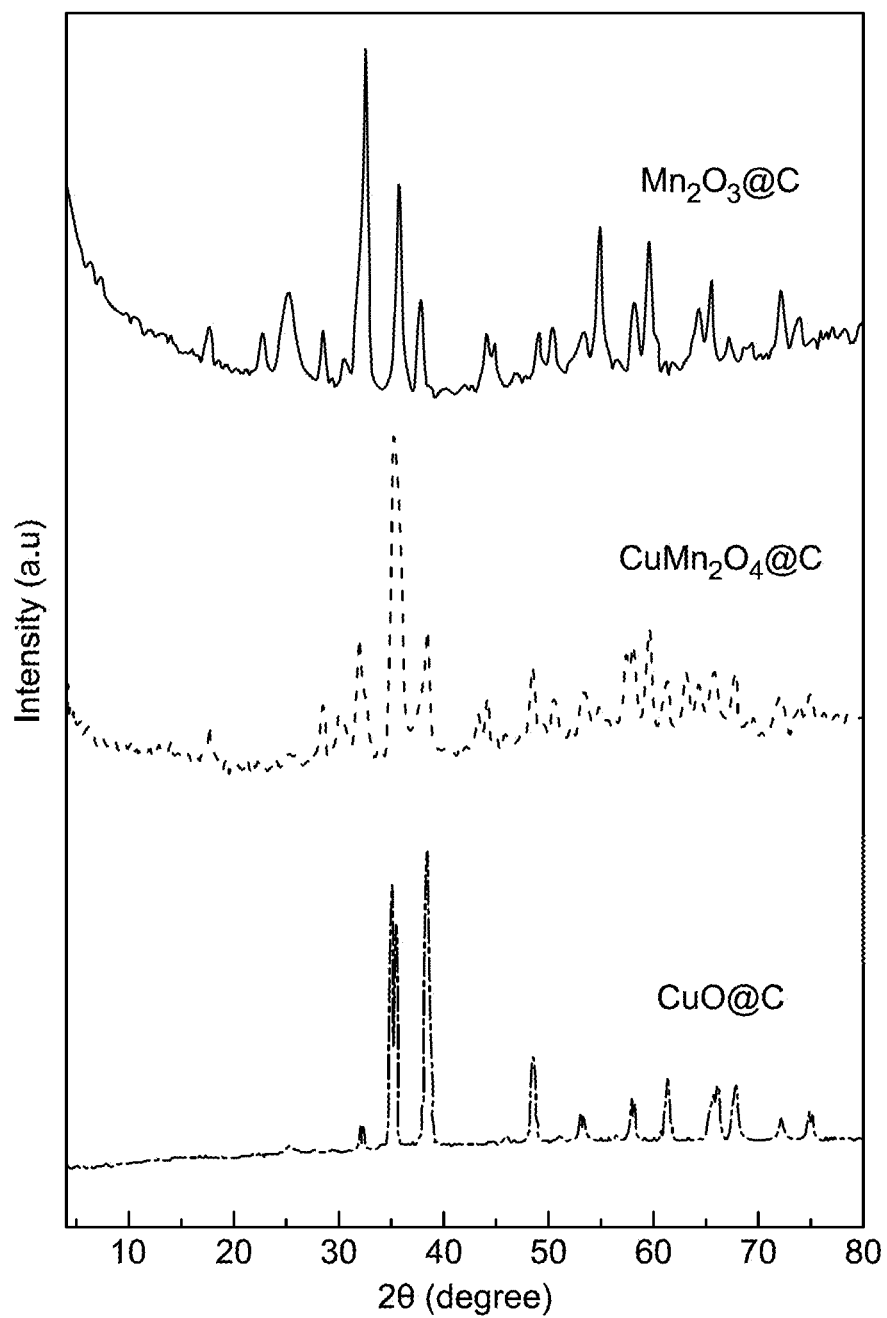
FIG. 6 shows X-ray diffraction (XRD) diffractograms of CuO@C metal-organic framework (MOF), $Mn_2O_3$@C MOF, and $CuMn_2O_3$@C MOF, calcined at 400° C., according to certain embodiments.

Referring to FIG. 6, XRD diffractograms of pure CuO@C, pure $Mn_2O_3$@C, and $CuMn_2O_4$@C calcined at 400° C., are shown, respectively. As can be seen from FIG. 6, the diffraction lines present in CuO@C sample after calcination when compared with the lines identified in the JCPDS no. 04-015-5877 cards—the disclosures of which are herein incorporated by reference in their entirety-reveal that these lines are corresponding to a monoclinic phase of CuO. The matching of the diffraction lines of pure $Mn_2O_3$@C annealed at 400° C. with that examined in the JCPDS no. 00-06-0540 cards—the disclosures of which are herein incorporated by reference in their entirety-depicted that the principal diffracted lines situated related to the tetragonal $Mn_2O_3$ lattice. In contrast, examination of the patterns of $CuMn_2O_4$@C mixtures calcined at 400° C. revealed that the diffractions are assigned to the $CuMn_2O_4$ (JCPDS No. 01-074-1921 and 00-045-0505 cards, the disclosures of which are herein incorporated by reference in their entirety) together with traces of CuO, and $Cu_{0.45}Mn_{0.55}O_2$ (JCPDS Card No. 00-041-0184 the disclosures of which is herein incorporated by reference in its entirety).

In order to evaluate the chemical composition and a plurality of oxidation states of the different element present in the $CuMn_2O_4$@C, XPS analysis was carried out for the $CuMn_2O_4$@C catalyst calcined at 400° C., as shown in FIGS. 7A-7E. The binding energies in the analysis were adjusted using C 1s at a potential of about 284.6 electron volts (eV) as a reference. The XPS survey, as shown in FIG. 7A, depicted the presence of Cu, Mn, O, and C. Further, as shown in FIG. 7B, high resolution XPS spectrum of Cu 2p indicates that Cu atoms in $CuMn_2O_4$ exist in flexible valence states of $Cu^+$ and $Cu^{2+}$ with respect to the Cu 2p orbit. $Cu^+$ of the spinel tetrahedron may be responsible for satellite peaks centered at 930.7 eV, whereas $Cu^{2+}$ is responsible for peaks centered at 934.0 eV and 962.3 eV.

FIG. 7C illustrates high-resolution XPS spectrum of Mn 2p in the $CuMn_2O_4$ product, in which the binding energy peaks at 653.1 eV and 641.7 eV refer to Mn 2p1/2 and Mn 2p3/2 of octahedral $Mn^{3+}$ ions in the $CuMn_2O_4$ spinel. The binding energy peaks located at 655.2 eV and 643.5 eV are related to Mn 2p1/2 and Mn 2p3/2 of octahedral $Mn^{4+}$ ions. However, the intensity and areas of peaks related to $Mn^{3+}$ is higher than that related to $Mn^{4+}$, indicating the majority of Mn in the spinel phase are $Mn^{3+}$. The high-resolution O 1s XPS spectrum, as shown in FIG. 7D, revealed the presence of peaks at 529.6 eV, and 531.2 eV. The aforementioned peaks correspond to the metal-oxygen bond (Or), and adsorbed oxygen (Ou), in the spinel $CuMn_2O_4$ nanomaterial, respectively (See: Y. Gao, B. Li, Z. Zhang, X. Zhang, Z. Deng, L. Huo, S. Gao, $CuMn_2O_4$ spinel nanoflakes for amperometric detection of hydrogen peroxide, the disclosure of which is incorporated herein in its entirety). Analysis of C 1s shows peaks at 284.2 eV, 286.4 eV, and 288.0 eV referring to C—C, C—O—C and O—C—O, respectively, as shown in FIG. 7E. It may be concluded that as per the results of XRD, and XPS analyses confirmed the fabrication of $CuMn_2O_4$@C.

Figure 8:
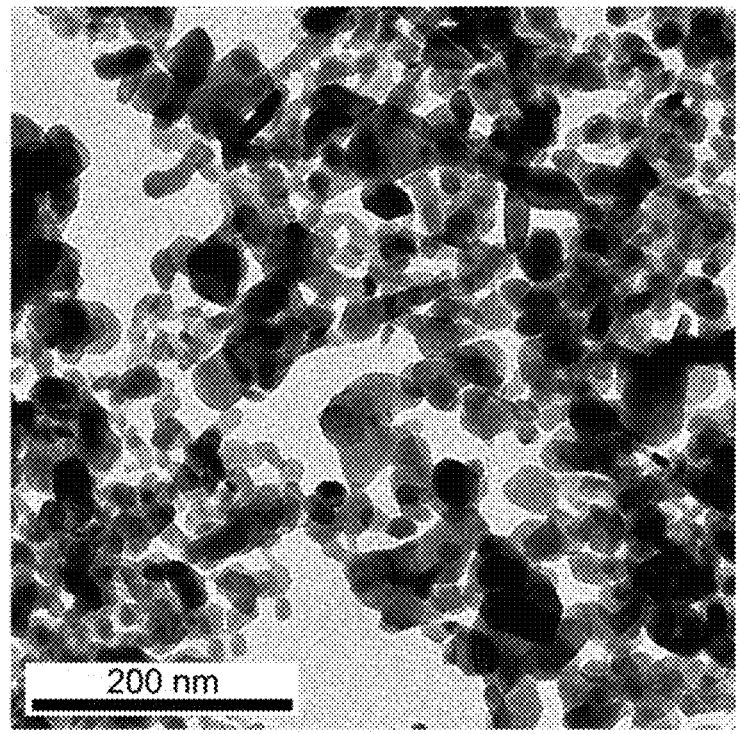
FIG. 8 shows a transmission electron microscopy (TEM) image of $CuMn_2O_4$@C, calcined at 400° C., according to certain embodiments.

In addition, morphology and particle size were evaluated using TEM images, as shown in FIG. 8. As can be seen from FIG. 8, a layer of carbon, which is core shell of $CuMn_2O_4$@C, formed, and coated the dark particle of $CuMn_2O_4$. Moreover, irregular spherical particles of $CuMn_2O_4$ with uniform distribution were seen in the TEM analysis.

According to the present disclosure, $CuMn_2O_4$@C nano catalysts derived from MOF were fabricated via the method described herein, followed by calcination at a temperature ranging from about 400° C. to 600° C. The synthesized catalyst herein, was characterized by XRD, XPS and TEM analyses. XRD and XPS analyses confirmed the formation of $CuMn_2O_4$@C. Further, the present disclosure describes the fabrication of the $CuMn_2O_4$ catalysts for the generation of the MEK biofuel. Catalytic activity results revealed that the fabricated catalyst was able to dehydrogenate butan-2-ol vapors selectively to MEK. Furthermore, various factors affecting the catalytic activity and selectivity were evaluated. The above-mentioned factors include reaction temperature, percentage of butan-2-ol in the reacting stream, calcination temperature, and reacting atmosphere. Basicity of the catalysts were measured by isopropyl alcohol dehydrogenation and hydrazine techniques and the results revealed that the $CuMn_2O_4$ catalyst calcined at 400° C. may be a highly active catalyst, providing a complete conversion and 100% selectivity at a temperature of about 250° C.

Numerous modifications and variations of the present disclosure are possible in light of the above teachings. It is, therefore, to be understood that within the scope of the appended claims, the invention may be practiced otherwise than as specifically described herein.

The invention claimed is:

1. A method of preparing nanoparticles of carbon-supported copper manganite ($CuMn_2O_4$), the method comprising:
preparing a first solution of a copper (II) salt and a manganese salt in a first polar organic solvent, wherein the molar ratio of Cu:Mn is from about 0.8:1 to about 1.2:1;
admixing a second solution of an organic ligand in a second polar organic solvent with the first solution to form a first mixture, wherein the second polar organic solvent is miscible with said first polar organic solvent;
hydrothermally heating the first mixture at a temperature of from about 100° C. to about 200° C. for a sufficient duration to form a solid metal-organic framework composite material; and,
calcining said metal-organic framework composite material at a temperature of from about 350 to about 600° C.,
wherein the copper manganite ($CuMn_2O_4$) of the nanoparticles has a crystalline spinel lattice which comprises copper in each of the $Cu^+$ and $Cu^{2+}$ oxidation states and comprises manganese in each of the $Mn^{3+}$ and $Mn^{4+}$ oxidation states; and,
further wherein a fraction of the nanoparticles have a core-shell morphology in which a shell of elemental carbon at least partially encapsulates a core nanoparticle of copper manganite ($CuMn_2O_4$).

2. The method according to claim 1, wherein the copper salt is selected from the group consisting of copper (II) sulfate ($CuSO_4$), copper (II) nitrate ($Cu(NO_3)_2$, copper (II) chloride ($CuCl_2$) and copper (II) acetate ($Cu(CH_3COO)$ 2).

3. The method according to claim 2, wherein the copper salt is copper (II) nitrate ($Cu(NO_3)_2$).

4. The method according to claim 1, wherein the manganese salt is selected from the group consisting of manganese sulfate ($MnSO_4$), manganese nitrate ($Mn(NO_3)_2$), manganese chloride ($MnCl_2$) and manganese acetate (Mn $(CH_3COO)_2$).

5. The method according to claim 4, wherein the manganese salt is manganese chloride ($MnCl_2$).

6. The method according to claim 1, wherein the molar ratio of Cu:Mn in the first solution is from about 0.9:1 to about 1.1:1.

7. The method according to claim 1, wherein the first polar organic solvent comprises at least one compound selected from the group consisting of dimethylformamide, diethylformamide, acetonitrile, methanol, ethanol, isopropanol, 1-butanol and acetone.

8. The method according to claim 1, wherein the first polar organic solvent comprises dimethylformamide and ethanol.

9. The method according to claim 1, wherein the second polar organic solvent comprises at least one compound selected from the group consisting of dimethylformamide, diethylformamide, acetonitrile, methanol, ethanol, isopropanol, 1-butanol and acetone.

10. The method according to claim 1, wherein the second polar organic solvent consists of dimethylformamide.

11. The method according to claim 1, wherein the organic ligand comprises at least one polycarboxylic acid.

12. The method according to claim 11, wherein the organic ligand comprises at least one dicarboxylic acid selected from the group consisting of ethanedioic acid, propanedioic acid, fumaric acid, benzene-1,4-dicarboxylic acid, benzene-1,3-dicarboxylic acid, benzene-1,2-dicarboxylic acid, 2,2'-bipyridine-5,5'-dicarboxylic acid and 2,2'-bipyridine-4,4'-dicarboxylic acid.

13. The method according to claim 11, wherein the organic ligand comprises at least one aromatic dicarboxylic acid selected from the group consisting of benzene-1,4-dicarboxylic acid, benzene-1,3-dicarboxylic acid, benzene-1,2-dicarboxylic acid, 2,2'-bipyridine-5,5'-dicarboxylic acid and 2,2'-bipyridine-4,4'-dicarboxylic acid.

14. The method according to claim 11, wherein the organic ligand consists of benzene-1,4-dicarboxylic acid.

15. The method according to claim 1, wherein the calcination temperature is from about 350° C. to about 450° C.

16. Nanoparticles of carbon-supported copper manganite ($CuMn_2O_4$) obtained according to the method defined in claim 1.

17. The method of claim 1, further comprising:
dehydrogenating gaseous butan-2-ol at a temperature of from about 200° C. to about 400° C. in the presence of nanoparticles of the carbon-supported copper manganite obtained according to the method as defined in claim 1 to form methyl ethyl ketone (MEK), wherein the gaseous butan-2-ol is carried in an inert gas.

18. The method according to claim 17, wherein the dehydrogenation temperature is from about 250° C. to about 400° C.

19. The method according to claim 17, wherein the inert gas consists essentially of nitrogen.

* * * * *